(12) United States Patent
Koch, Jr. et al.

(10) Patent No.: US 11,701,136 B2
(45) Date of Patent: Jul. 18, 2023

(54) UNCLAMP LOCKOUT MECHANISM FOR A SURGICAL TOOL

(71) Applicant: Cilag GmbH International, Zug (CH)

(72) Inventors: Robert Louis Koch, Jr., Cincinnati, OH (US); Mark D. Overmyer, Cincinnati, OH (US); Christopher A. Denzinger, Cincinnati, OH (US); Kris Eren Kallenberger, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1117 days.

(21) Appl. No.: 16/385,426

(22) Filed: Apr. 16, 2019

(65) Prior Publication Data

US 2020/0330120 A1    Oct. 22, 2020

(51) Int. Cl.
*A61B 17/32* (2006.01)
*A61B 17/28* (2006.01)
(Continued)

(52) U.S. Cl.
CPC .... *A61B 17/320016* (2013.01); *A61B 17/068* (2013.01); *A61B 17/28* (2013.01); *A61B 17/3201* (2013.01); *A61B 18/1445* (2013.01); *A61B 34/37* (2016.02); *A61B 90/361* (2016.02); *A61B 2017/00407* (2013.01);
(Continued)

(58) Field of Classification Search
CPC .............. A61B 17/068; A61B 17/0682; A61B 17/0684; A61B 17/0686; A61B 17/072; A61B 17/115; A61B 17/128; A61B 17/1285; A61B 17/28; A61B 17/295; A61B 17/320016; A61B 17/3201;
(Continued)

(56) References Cited

U.S. PATENT DOCUMENTS

2017/0143362 A1\* 5/2017 Cagle ................. A61B 18/1445
2017/0281179 A1\* 10/2017 Shelton, IV ......... A61B 17/115
(Continued)

FOREIGN PATENT DOCUMENTS

WO    2017172716 A1    10/2017
WO    2019123170 A1    6/2019

OTHER PUBLICATIONS

ISR/WO for PCT/IB2020/053566, which claims priority to the present application, dated Jul. 16, 2020.

*Primary Examiner* — Diane D Yabut
(74) *Attorney, Agent, or Firm* — Vorys, Safer, Seymour and Pease LLP

(57) ABSTRACT

A surgical tool includes a drive housing, a shaft extending from the drive housing, an end effector at an end of the shaft and having opposing jaws and a cutting element, and an unclamp lockout mechanism. The unclamp lockout mechanism including a pawl rotatably mounted to the shaft and positioned proximal to a closure yoke operatively coupled to the shaft, the pawl being pivotable between a stowed position, where the pawl is received within an aperture of the shaft, and a deployed position, where the pawl protrudes out of the aperture, and a biasing device that biases the pawl toward the stowed position. When the pawl is in the stowed position, the closure yoke is movable to a proximal position over at least a portion of the pawl to open the opposing jaws. When the pawl is in the deployed position, the closure yoke is prevented from moving to the proximal position.

20 Claims, 10 Drawing Sheets

(51) Int. Cl.
  *A61B 34/37*      (2016.01)
  *A61B 90/00*      (2016.01)
  *A61B 17/068*     (2006.01)
  *A61B 17/3201*    (2006.01)
  *A61B 18/14*      (2006.01)
  *A61B 17/00*      (2006.01)
  *A61B 18/00*      (2006.01)
  *A61B 18/12*      (2006.01)

(52) U.S. Cl.
  CPC ............... *A61B 2018/0063* (2013.01); *A61B 2018/00595* (2013.01); *A61B 2018/126* (2013.01)

(58) Field of Classification Search
  CPC .. A61B 2017/07285; A61B 2017/2946; A61B 2017/320097; A61B 18/1445
  See application file for complete search history.

(56) References Cited

U.S. PATENT DOCUMENTS

2017/0296173 A1   10/2017   Shelton, IV
2018/0168597 A1    6/2018   Fanelli

\* cited by examiner

UNCLAMP LOCKOUT MECHANISM FOR A SURGICAL TOOL

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long, shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Surgical staplers are one type of end effector capable of cutting and simultaneously stapling (fastening) transected tissue. Alternately referred to as an "endocutter," the surgical stapler includes opposing jaws capable of opening and closing to grasp and release tissue. Once tissue is grasped or clamped between the opposing jaws, the end effector may be "fired" to advance a cutting element or knife distally to transect grasped tissue. As the cutting element advances, staples contained within the end effector are progressively deployed to seal opposing sides of the transected tissue.

If the surgical stapler is fired (or partially fired) and subsequently loses power, or the jaws are somehow inadvertently opened, the knife may potentially be exposed and could inadvertently cut patient tissue or a user. What is needed is a device or system that prevents the knife from being driven distally until the jaws are properly clamped in the closed position, and such a device or system would also prevent the jaws from opening until the knife has been safely retracted.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgery and, more particularly, to an unclamp lockout mechanism used to manage when opposing jaws can be opened and manage when the cutting element can be advanced to avoid inadvertent exposure of a cutting element.

The embodiments described herein discuss a spring biased unclamp lockout mechanism arranged in in the shaft assembly of a surgical tool. The unclamp lockout mechanism may be moved between stowed and deployed positions as acted upon by a firing rod that actuates a cutting element of the surgical tool. One example surgical tool includes a drive housing, a shaft extending from the drive housing, an end effector at an end of the shaft and having opposing jaws and a cutting element, and an unclamp lockout mechanism. The unclamp lockout mechanism may include a pawl rotatably mounted to the shaft and positioned proximal to a closure yoke, which is operatively coupled to the shaft. The pawl may be pivotable between a stowed position, where the pawl is received within an aperture of the shaft, and a deployed position, where the pawl protrudes out of the aperture. A biasing device may bias the pawl toward the stowed position and, when the pawl is in the stowed position, the closure yoke is movable to a proximal position over at least a portion of the pawl to open the opposing jaws. Moreover, when the pawl is in the stowed position, the firing rod may be prevented from moving distally, thereby preventing the cutting element from advancing and exposing it. In contrast, when the pawl is in the deployed position, the closure yoke may be prevented from moving to the proximal position and potentially exposing the cutting element.

Figure 1:
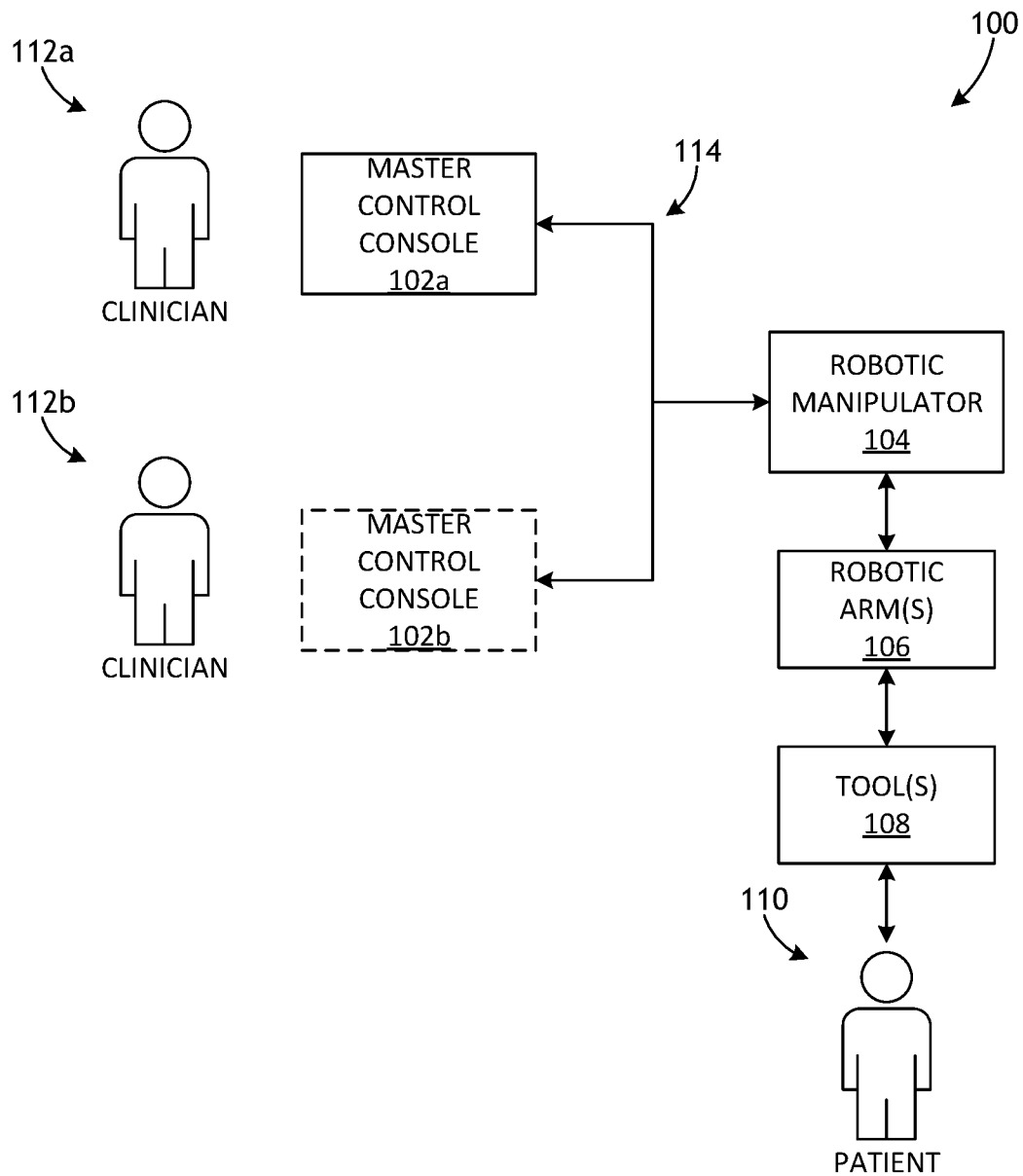
FIG. 1 is a block diagram of an example robotic surgical system that may incorporate some or all of the principles of the present disclosure.
Figure 3:
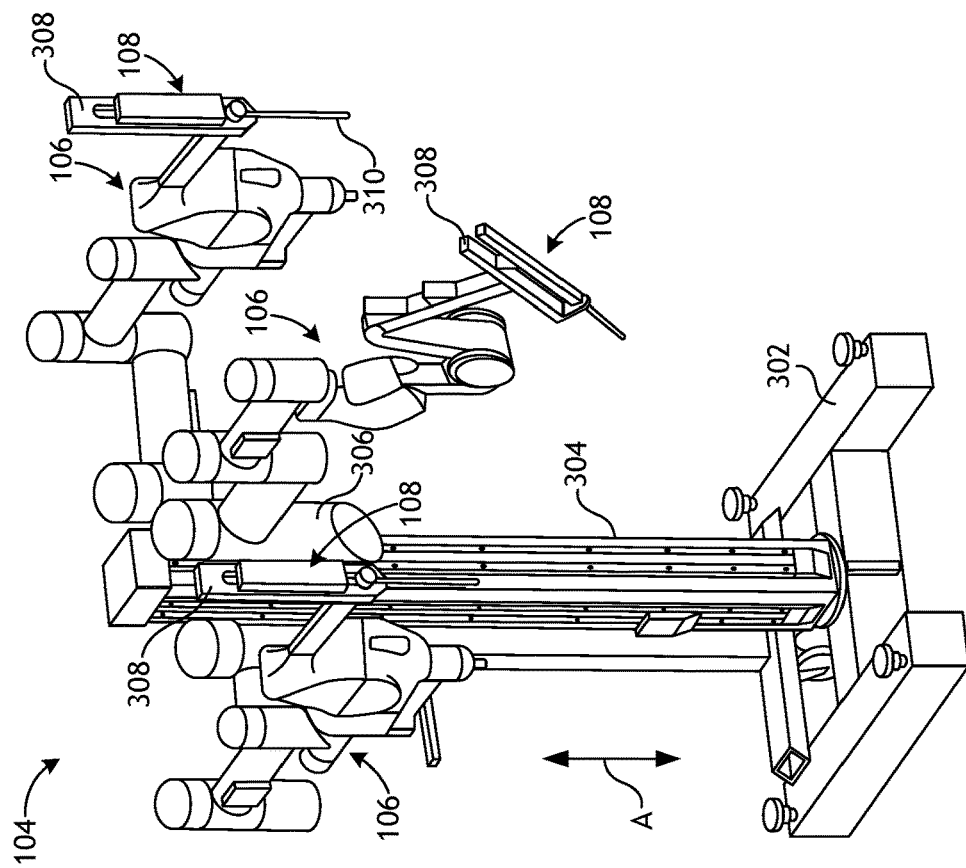
FIG. 3 depicts one example of the robotic manipulator of FIG. 1, according to one or more embodiments.
Figure 2:
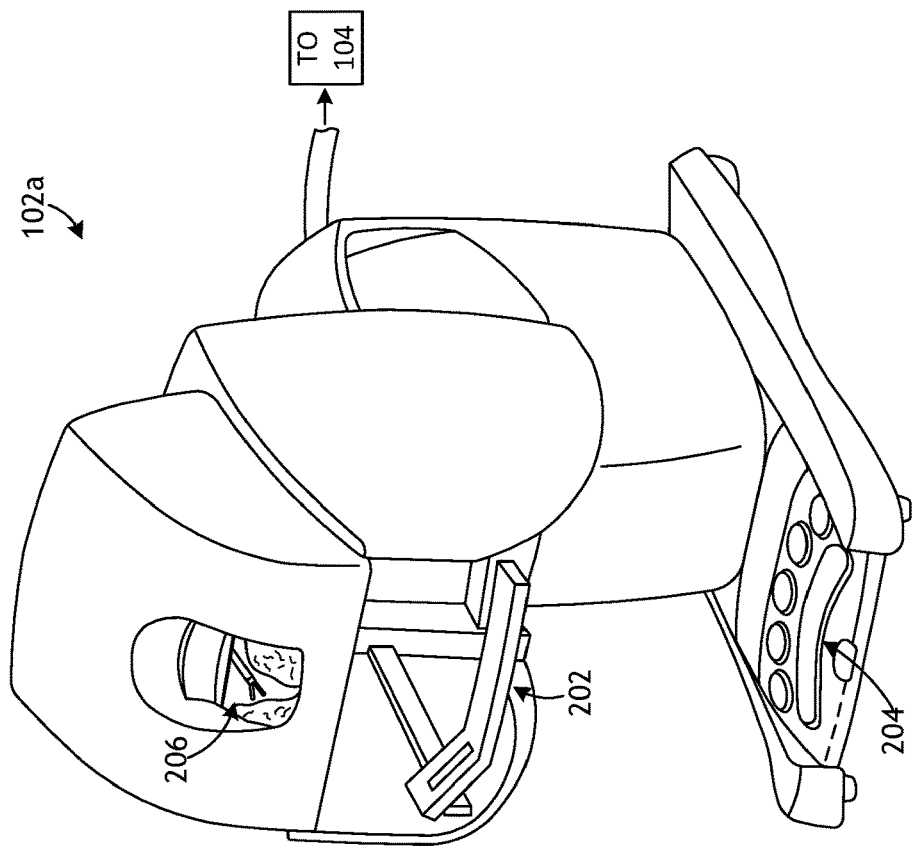
FIG. 2 is an example embodiment of one of the master control consoles of FIG. 1.

FIGS. 1-3 illustrate the structure and operation of an example robotic surgical system and associated components thereof. While applicable to robotic surgical systems, it is noted that the principles of the present disclosure may equally or alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping two user input devices (not shown), one in each hand. The user input devices can comprise, for example, physical controllers such as, but not limited to, a joystick, exoskeletal gloves, a master manipulator, etc., and may be movable in multiple degrees of freedom to control the position and operation of the surgical tool(s) 108 (FIG. 1). In some embodiments, the master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or castors to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

Figure 4:
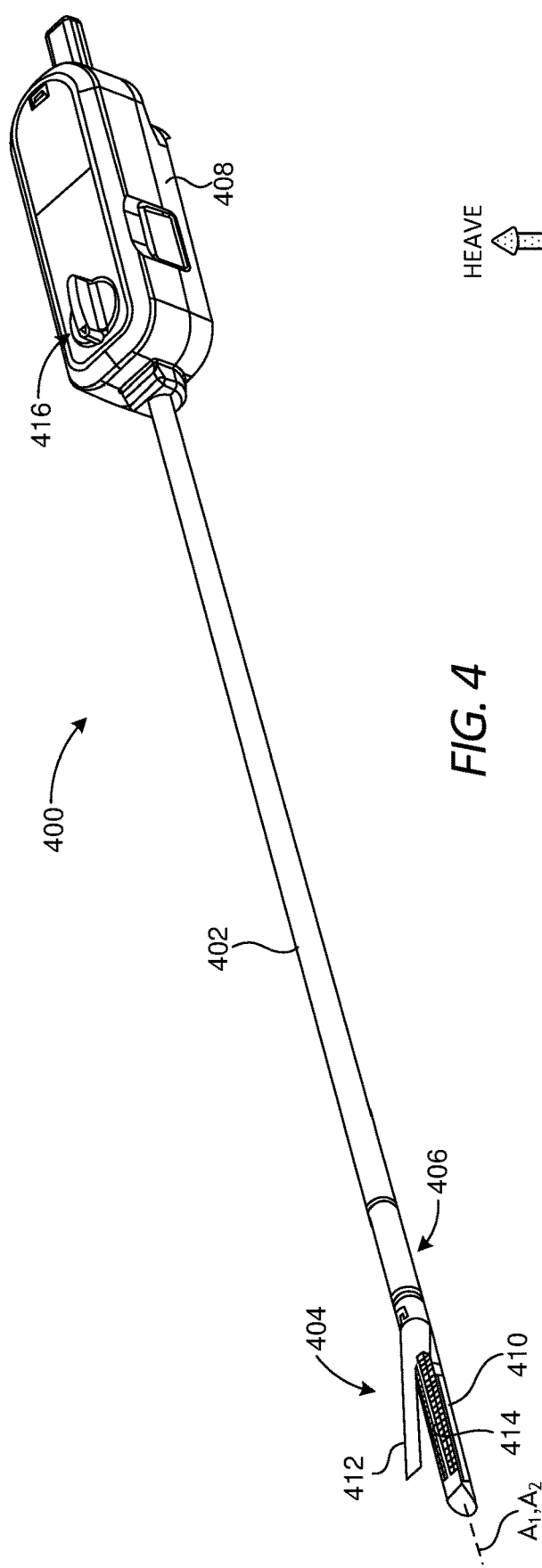
FIG. 4 is an isometric side view of an example surgical tool that may incorporate some or all of the principles of the present disclosure.

FIG. 4 is an isometric side view of an example surgical tool 400 that may incorporate some or all of the principles of the present disclosure. The surgical tool 400 may be the same as or similar to the surgical tool(s) 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. The principles of the present disclosure, however, are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. In the illustrated embodiment, the end effector 404 comprises a surgical stapler, alternately referred to as an "endocutter," configured to cut and staple (fasten) tissue. As illustrated, the end effector 404 includes opposing jaws 410, 412 configured to move (articulate) between open and closed positions. The opposing jaws 410, 412, however, may alternately form part of other types of end effectors with jaws such as, but not limited to, a tissue grasper, surgical scissors, an advanced energy vessel sealer, a clip applier, a needle driver, a babcock including a pair of opposed grasping jaws, bipolar jaws (e.g., bipolar Maryland grasper, forceps, a fenestrated grasper, etc.), etc. One or both of the jaws 410, 412 may be configured to pivot to actuate the end effector 404 between the open and closed positions.

In the illustrated embodiment, the first jaw 410 may be characterized or otherwise referred to as a "cartridge" jaw, and the second jaw 412 may be characterized or otherwise referred to as an "anvil" jaw. More specifically, the first jaw 410 may include a frame that houses or supports a staple cartridge, and the second jaw 412 is pivotally supported relative to the first jaw 410 and defines a surface that operates as an anvil to form staples ejected from the staple cartridge during operation. In use, the second jaw 412 is rotatable between an open, unclamped position and a closed, clamped position. In other embodiments, however, the first jaw 410 may move (rotate) relative to the second jaw 412, without departing from the scope of the disclosure.

Figure 5:
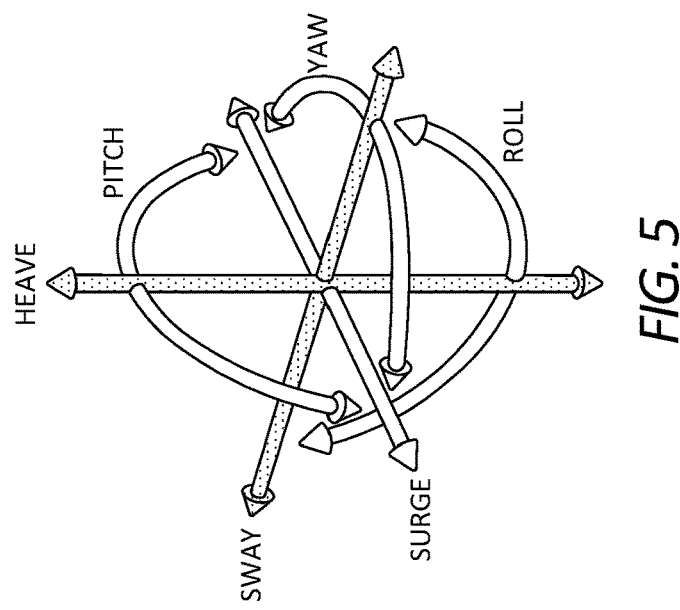
FIG. 5 illustrates potential degrees of freedom in which the wrist of FIG. 4 may be able to articulate (pivot).

The wrist 406 enables the end effector 404 to articulate (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may include a plurality of drive members or the like (obscured in FIG. 4) that form part of an actuation system configured to facilitate articulation of the wrist 406 and actuation (operation) of the end effector 404 (e.g., clamping, firing, rotation, articulation, energy delivery, etc.). Some drive members may extend to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). In the illustrated embodiment, actuating the end effector 404 may comprise closing and/or opening the second jaw 412 relative to the first jaw 410 (or vice versa), thereby enabling the end effector 404 to grasp (clamp) onto tissue. In addition, once tissue is grasped or clamped between the opposing jaws 410, 412, actuating the end effector 404 may further comprise "firing" the end effector 404, which may refer to causing a cutting element or knife (not visible) to advance distally within a slot 414 defined in the second jaw 410. As it moves distally, the cutting element may transect any tissue grasped between the opposing jaws 410, 412. Moreover, as the cutting element advances distally, a plurality of staples contained within the staple cartridge (i.e., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue.

In some embodiments, the surgical tool 400 may be configured to apply energy to tissue, such as radio frequency (RF) energy. In such cases, actuating the end effector 404 may further include applying energy to tissue grasped or clamped between two opposing jaws to cauterize or seal the captured tissue, following which the tissue may be transected.

In some embodiments, the surgical tool 400 may further include a manual closure device 416 accessible to a user on the exterior of the drive housing 408. As illustrated, the manual closure device 416 may comprise a knob that may be grasped by the user. The manual closure device 416 may be operatively coupled to various gears and/or drive members within the drive housing 408 to allow a clinician to manually open and close the jaws 410, 412. In some cases, a clinician may be able to fully clamp and fully unclamp the jaws 410, 412 with the manual closure device 416. The manual closure device 416 may be particularly useful to a clinician when the surgical tool 400 is detached from a surgical robot, since having the capability to open and close the jaws 410, 412 may eliminate the need to place inadvertent stress on internal drive members or components. In the event that a clinician desires to manually open the jaws 410, 412 when the surgical tool 400 is still attached to a surgical robot, the clinician can rotate the manual closure device 416 in an attempt to open the end effector 404.

Figure 6:
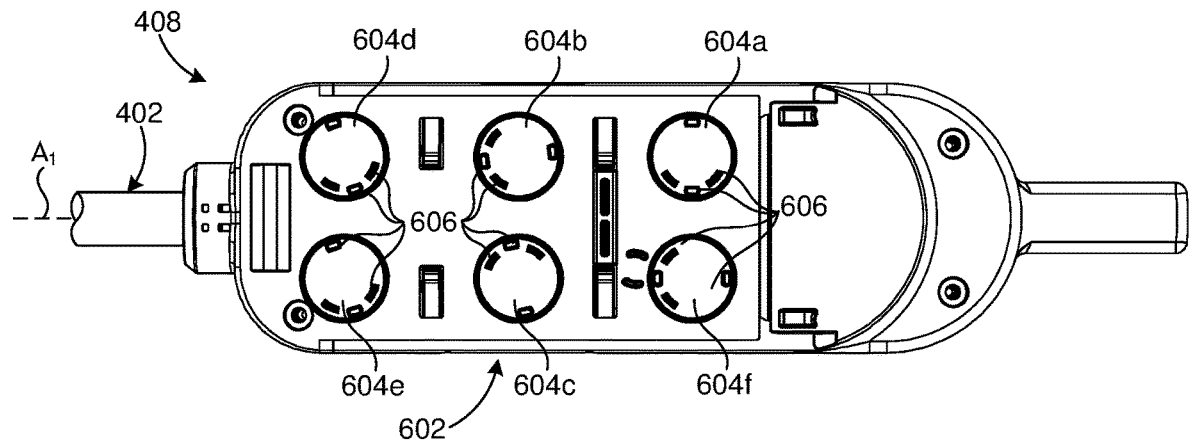
FIG. 6 is a bottom view of the drive housing of FIG. 4, according to one or more embodiments.

FIG. 6 depicts a bottom view of the drive housing 408, according to one or more embodiments. As illustrated, the drive housing 408 (alternately referred to as a "puck") may include a tool mounting portion 602 used to operatively couple the drive housing 408 to a tool driver (e.g., the tool drivers 308 of FIG. 3), and may thus be operable in conjunction with any of the robotic manipulators mentioned herein. The tool mounting portion 602 includes and otherwise provides an interface that mechanically, magnetically, and/or electrically couples the drive housing 408 to the tool driver. In at least one embodiment, the tool mounting portion 602 couples the drive housing 408 to the tool driver via a sterile barrier (not shown).

As illustrated, the tool mounting portion 602 includes and supports a plurality of inputs, shown as drive inputs 604a, 604b, 604c, 604d, 604e, and 604f. Each drive input 604a-f may comprise a rotatable disc configured to align and mate with a corresponding driver or "drive disc" included in the tool driver. Each drive input 604a-f may provide or define one or more surface features 606 configured to mate with corresponding features provided on the drive discs to facilitate operative engagement between the opposing structures such that movement of a given drive disc correspondingly moves the associated drive input 604a-f.

In some embodiments, actuation of the first drive input 604a may control rotation of the shaft 402 about its longitudinal axis $A_1$. More particularly, depending on the rotational direction of the first drive input 604a, the shaft 402 can be rotated clockwise or counter-clockwise, thus correspondingly rotating the end effector 404 (FIG. 4). Actuation of the second and third drive inputs 604b,c may control articulation of the end effector 404 at the wrist 406 (FIG. 4). Actuation of the fourth and fifth drive inputs 604d,e may cause an outer portion of the shaft 402 (referred to herein as a "closure tube") to advance and retract, which closes and opens the jaws 410, 412 (FIG. 4). Lastly, actuation of the sixth drive input 604f may cause the end effector 404 to fire, which may entail distal deployment of a cutting element to transect tissue grasped by the jaws 410, 412 and simultaneous deployment of staples contained within the staple cartridge housed within the first jaw 410.

Figure 7A:
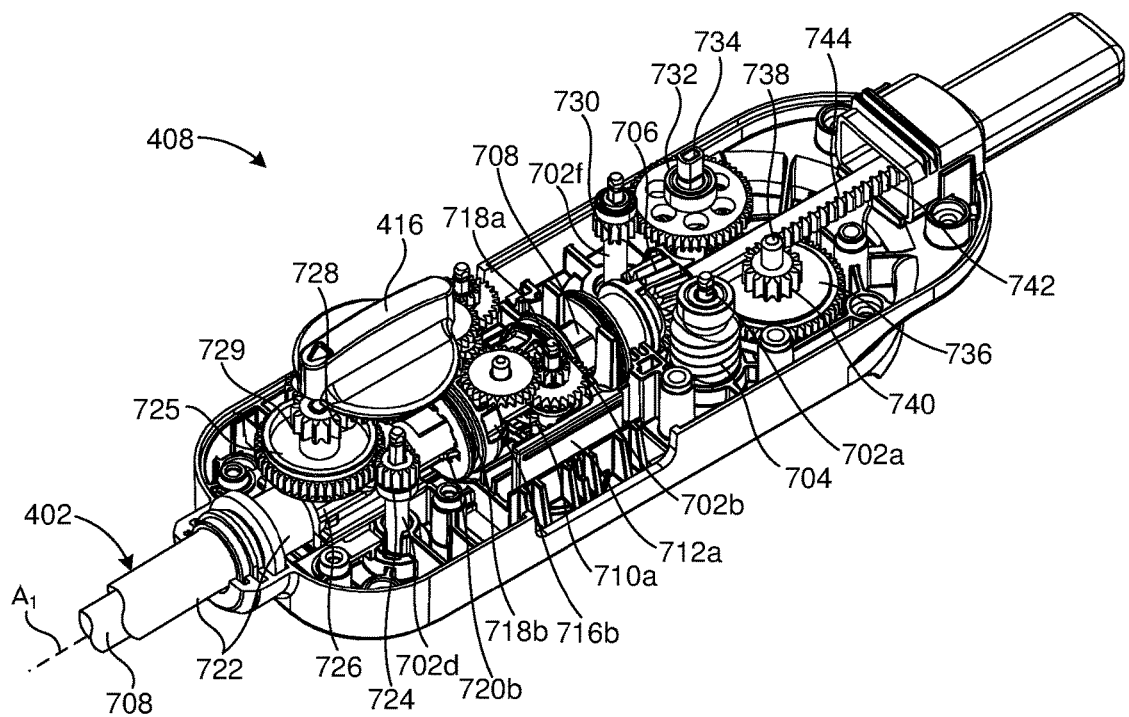
FIGS. 7A and 7B are exposed isometric views of the interior of the drive housing of FIG. 4, according to one or more embodiments.
Figure 7B:
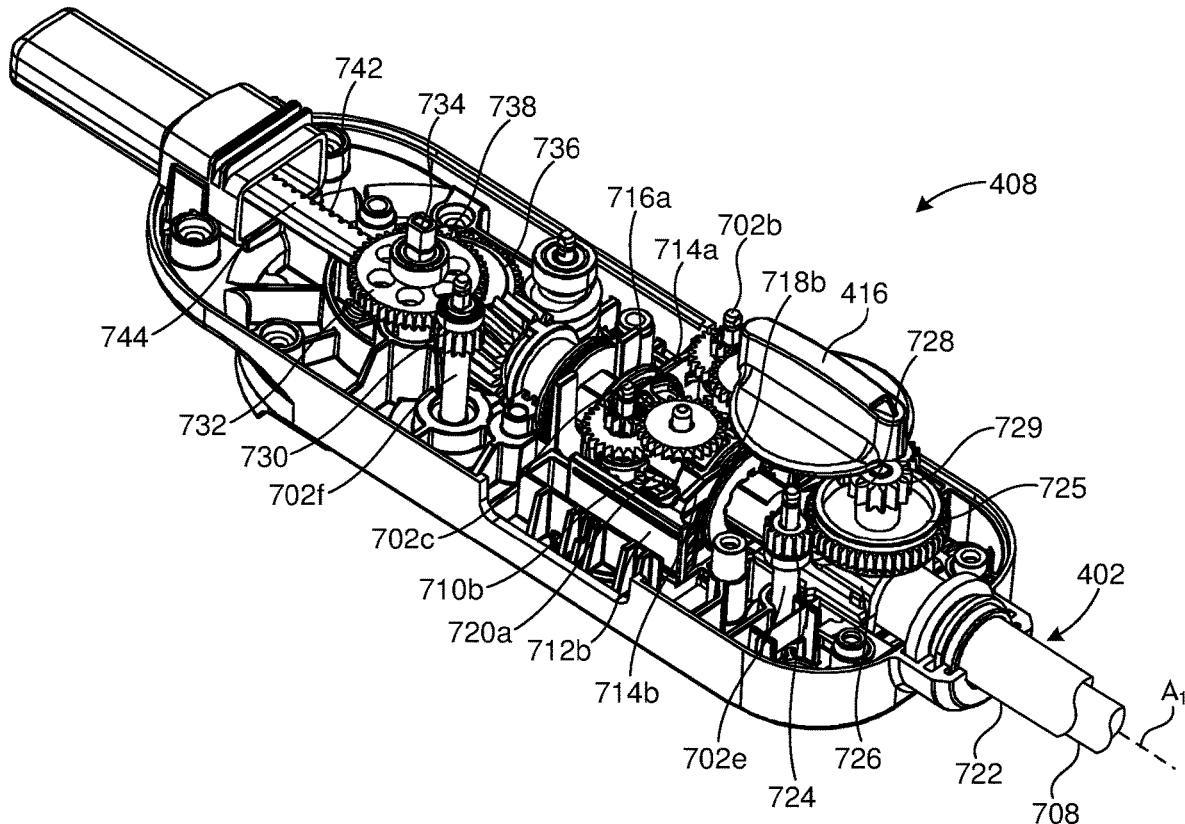

Referring to FIGS. 7A and 7B, illustrated are exposed isometric views of the interior of the drive housing 408, according to one or more embodiments. The upper portion of the drive housing 408 is omitted in FIGS. 7A-7B to allow viewing of the internal working components and parts. In addition, several component parts that would otherwise be included within the drive housing 408 are omitted in FIGS. 7A-7B to simplify the figures and enable discussion of the depicted component parts.

Referring first to FIG. 7A, a first drive shaft 702a is coupled to the first drive input 604a (FIG. 6) such that actuation and rotation of the first drive input 604a correspondingly rotates the first drive shaft 702a. A helical drive gear 704 is coupled to the first drive shaft 702a and rotates as the first drive shaft 702a rotates. The helical drive gear 704 intermeshes with a helical driven gear 706, which is operatively coupled to the shaft 402 and, more particularly, to an inner grounding shaft 708 that forms part of the shaft 402. The inner grounding shaft 708 extends concentrically within an outer portion of the shaft 402 referred to herein as the "closure tube." Accordingly, actuation of the first drive input 604a drives the first drive shaft 702a and correspondingly drives the inner grounding shaft 708 to rotate the shaft 402 about the longitudinal axis $A_1$.

A second drive shaft 702b may be coupled to the second drive input 604b (FIG. 6) such that actuation and rotation of the second drive input 604b correspondingly rotates the second drive shaft 702b. A pinion gear 710a is attached to the second drive shaft 702b and is rotatable therewith. The pinion gear 710a intermeshes with a first driven rack 712a such that as the pinion gear 710a is rotated in a first rotational direction, the first driven rack 712a correspondingly translates in a first longitudinal direction. As the pinion gear 710a is rotated in a second rotational direction, the first driven rack 712a correspondingly translates in a second longitudinal direction opposite the first longitudinal direction.

As best seen in FIG. 7B, the first driven rack 712a includes a first fork 714a matable with a first articulation yoke 716a. More specifically, the first fork 714a is configured to be received within an annular slot 718a (FIG. 7A) defined in the first articulation yoke 716a, which allows the first articulation yoke 716a to rotate about the longitudinal axis $A_1$ as the inner grounding shaft 708 rotates. Moreover, engagement between the first fork 714a and the annular slot 718a allows the first driven rack 712a to drive the first articulation yoke 716a along the longitudinal axis $A_1$ (distally or proximally) as acted upon by rotation of the second drive shaft 702b. The first articulation yoke 716a may be coupled to a first drive member 720a, which extends distally to the wrist 406 (FIG. 4). Axial movement of the first articulation yoke 716a along the longitudinal axis $A_1$ correspondingly moves the first drive member 720a, which causes the wrist 406 and the end effector 404 (FIG. 4) to articulate.

Still referring to FIG. 7B, a third drive shaft 702c is coupled to the third drive input 604c (FIG. 6) such that actuation and rotation of the third drive input 604c correspondingly rotates the third drive shaft 702c. A pinion gear 710b is attached to the third drive shaft 702c and is rotatable therewith. The pinion gear 710b intermeshes with a second driven rack 712b such that rotating the pinion gear 710b in a first rotational direction correspondingly translates the second driven rack 712b in a first longitudinal direction. Rotating the pinion gear 710b in a second rotational direction correspondingly translates the second driven rack 712b in a second longitudinal direction opposite the first longitudinal direction.

The second driven rack 712b includes a second fork 714b matable with a second articulation yoke 716b (FIG. 7A). More particularly, the second fork 714b is configured to be received within an annular slot 718b defined in the second articulation yoke 716b, which allows the second articulation yoke 716b to rotate about the longitudinal axis $A_1$ as the inner grounding shaft 708 rotates. Moreover, engagement between the second fork 714b and the annular slot 718b allows the second driven rack 712*b* to drive the second articulation yoke 716*b* along the longitudinal axis $A_1$ (distally or proximally) as acted upon by rotation of the third drive shaft 702*c*. The second articulation yoke 716*b* may be coupled to a second drive member 720*b* (FIG. 7A), which extends distally to the wrist 406 (FIG. 4). Axial movement of the second articulation yoke 716*b* along the longitudinal axis $A_1$ correspondingly moves the second drive member 720*b*, which causes the wrist 406 and the end effector 404 (FIG. 4) to articulate.

Accordingly, axial movement of the first and second articulation yokes 716*a,b*, along the longitudinal axis $A_1$ cooperatively actuates the drive members 720*a,b* and, thereby, articulates the end effector 404. In at least one embodiment, the first and second articulation yokes 716*a,b* antagonistically operate such that one of the articulation yokes 716*a,b* pulls one of the drive members 720*a,b* proximally while the other articulation yoke 716*a,b* pushes the other drive member 720*a,b* distally. In at least one embodiment, however, the first and second articulation yokes 716*a,b* may be operated independently without the other being operated.

A fourth drive shaft 702*d* (FIG. 7A) and a fifth drive shaft 702*e* (FIG. 7B) may be coupled to the fourth and fifth drive inputs 604*d,e* (FIG. 6), respectively, such that actuation and rotation of the fourth and fifth drive inputs 604*d,e* correspondingly rotates the fourth and fifth drive shafts 702*d,e*. Rotation of the fourth and fifth drive shafts 702*d,e* may cause a portion of the shaft 402 to advance or retract. More specifically, the outer portion of the shaft 402 may comprise a closure tube 722 that is axially translated to move the jaws 410, 412 (FIG. 4) between open and closed positions. As illustrated, each drive shaft 702*d,e* has a spur gear 724 attached thereto, and both spur gears 724 are positioned to mesh with a primary drive gear 725 mounted to a closure yoke 726.

The closure yoke 726 is rotatably mounted to the closure tube 722 but fixed axially thereto. This allows the closure tube 722 to rotate as the inner grounding shaft 708 rotates, but also allows the closure yoke 726 to advance or retract the closure tube 722. A projection (not shown) extends from or is otherwise coupled to the closure yoke 726, and the projection interacts with the primary drive gear 725 to facilitate axial movement of the closure yoke 726. Accordingly, rotating the spur gears 724 causes the primary drive gear 725 to rotate, which correspondingly causes the closure yoke 726 and the interconnected closure tube 722 to axially translate.

The primary drive gear 725 may also be operatively coupled to the manual closure device 416 arranged on the exterior of the drive housing 408. As illustrated, the manual closure device 416 may include a drive gear 728 that intermeshes with a driven gear 729 mounted to the primary drive gear 725. Consequently, a user can grasp and rotate the manual closure device 416 to correspondingly rotate the primary drive gear 725 and thereby drive the drive gear 728 against the driven gear 729 to move the closure yoke 426 distally and proximally to close and open the jaws 410, 412 (FIG. 4), as generally described above.

Figure 8:
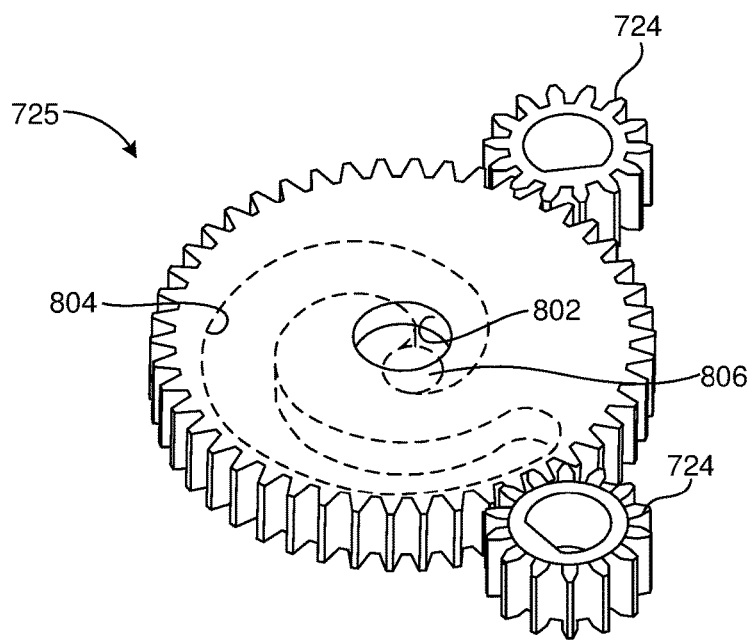
FIG. 8 depicts one example of a primary drive gear as intermeshed with the spur gears of FIGS. 7A-7B.

Referring to FIG. 8, illustrated is one example of the primary drive gear 725 as intermeshed with the spur gears 724. As illustrated, the primary drive gear 725 comprises a central aperture 802 that rotatably mounts the primary drive gear 725 within the drive housing 408 (FIGS. 7A-7B) relative to the spur gears 724. A spiral cam slot 804 is defined in the primary drive gear 725 and a projection 806 of the closure yoke 726 (FIGS. 7A-7B) is received therein.

The primary drive gear 725 is rotatable about an axis extending through the central aperture 802 as acted upon by the spur gears 724. As the primary drive gear 725 rotates, the projection 806 follows the spiral cam slot 804, and the curvature of the spiral cam slot 804 urges the interconnected closure yoke 726 to translate longitudinally relative to the primary drive gear 725. When the closure yoke 726 moves distally, the closure tube 722 (FIGS. 7A-7B) correspondingly moves in the distal direction and causes the jaws 410, 412 (FIG. 4) to close. In contrast, when the closure yoke 726 moves proximally, the closure tube 722 correspondingly moves in the proximal direction and causes the jaws 410, 412 to open.

Referring again to FIGS. 7A and 7B, a sixth drive shaft 702*f* is coupled to the sixth drive input 604*f* (FIG. 6) such that actuation and rotation of the sixth drive input 604*f* correspondingly rotates the sixth drive shaft 702*f*. Rotating the sixth drive shaft 702*f* may advance and retract a firing rod (not shown) that extends through the shaft 402 to the end effector 404 (FIG. 4). The distal end of the firing rod is operatively coupled to the cutting element (knife) such that axial movement of the firing rod correspondingly moves the cutting element distally or proximally to transect tissue grasped between the jaws 410, 412 (FIG. 4). In some embodiments, distal movement of the firing rod also deploys the staples, as described above.

A spur gear 730 is coupled to the sixth drive shaft 702*f* such that rotation of the sixth drive shaft 702*f* correspondingly rotates the spur gear 730. The spur gear 730 intermeshes with a second spur gear 732, which is attached to a first transfer drive shaft 734. A third spur gear (not visible) is coupled to the first transfer drive shaft 734 and intermeshes with a fourth spur gear 736, which is attached to a second transfer drive shaft 738. Finally, an output pinion gear 740 (FIG. 7A) is coupled to the second transfer drive shaft 738 and intermeshes with a rack gear 742 of a firing member 744 such that rotation of the output pinion gear 740 causes axial translation of the firing member 744. The firing member 744 may be coupled to the firing rod (not shown) discussed above. Accordingly, rotation of the sixth drive shaft 702*f* will drive the firing member 744 in axial translation, which correspondingly drives the firing rod in the same direction to advance and retract the cutting element at the end effector 404 (FIG. 4).

If the firing member 744 is moved and the firing rod fires (or partially fires) to distally extend the cutting element, and the tool loses power and/or the jaws 410, 412 (FIG. 4) are somehow forced open, the cutting element may become exposed and potentially cause inadvertent patient tissue damage or harm to the user. According to the present disclosure, the tool may include an unclamp lockout mechanism used prevent the closure tube 722 from retracting proximally to open the jaws 410, 412 (FIG. 4) until the firing member 744 and interconnected firing rod have been retracted to safely retract the cutting element. Once the cutting element has been retracted, the unclamp lockout mechanism may allow the closure tube 722 to move and open the jaws 410, 412, if desired. The unclamp lockout mechanism may be linked to the position of the cutting element such that it is able to be deployed when the cutting element is extended (fired) and stowed when the cutting element is retracted (homed).

Figure 9A:
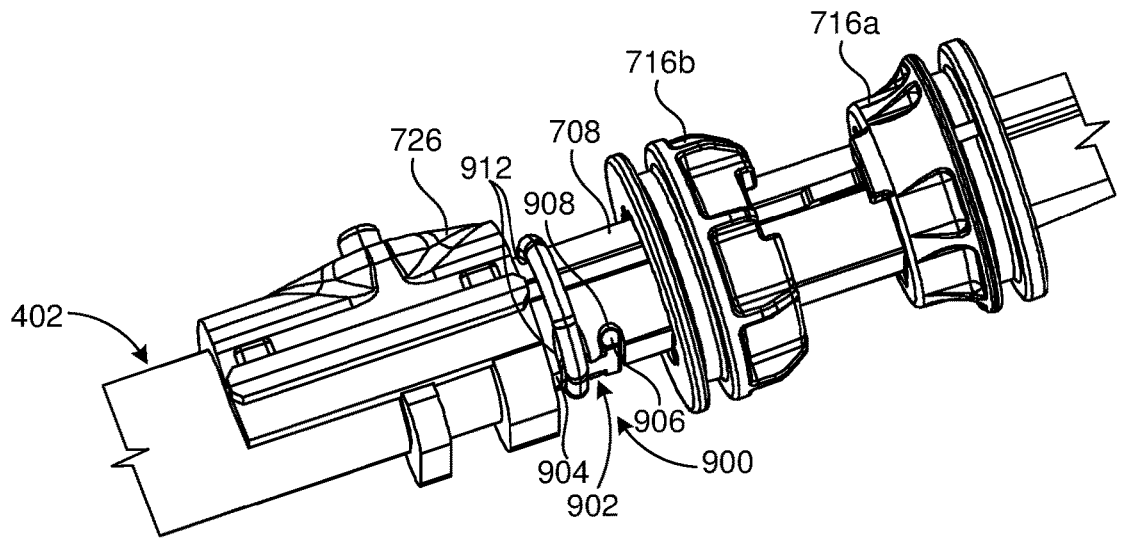
FIGS. 9A and 9B are isometric views of an example unclamp lockout mechanism, according to one or more embodiments of the disclosure.
Figure 9B:
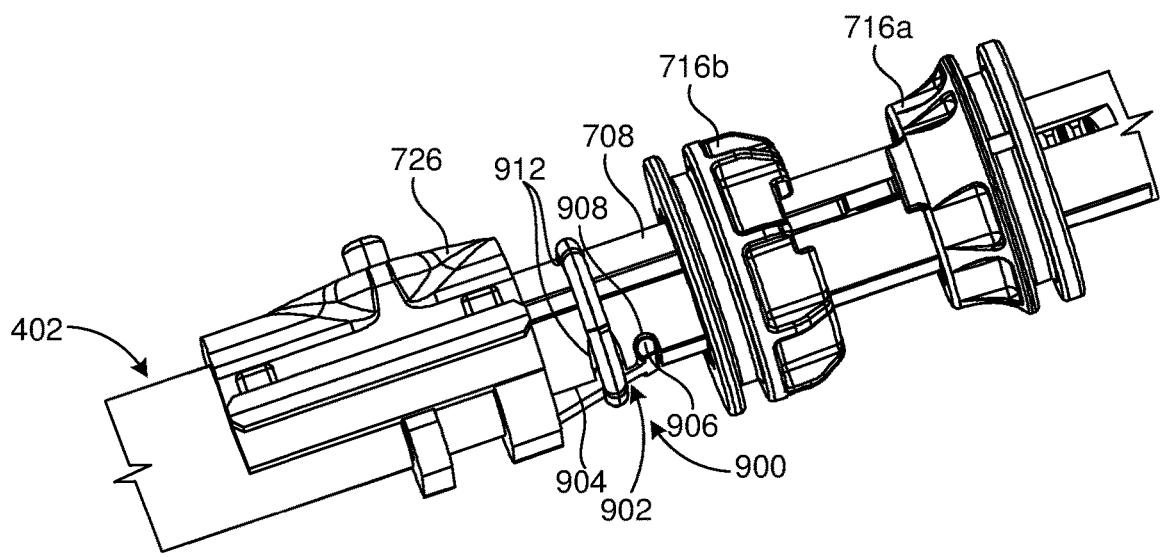

FIGS. 9A and 9B are isometric views of an example unclamp lockout mechanism 900, according to one or more embodiments of the disclosure. More specifically, FIG. 9A shows the unclamp lockout mechanism 900 in a stowed position, and FIG. 9B shows the unclamp lockout mechanism 900 in a deployed position. As illustrated, the unclamp lockout mechanism 900 may be arranged along the shaft 402 proximal to the closure yoke 726. More particularly, the unclamp lockout mechanism may interpose the articulation yokes 716a,b and the closure yoke 726. Accordingly, the unclamp lockout mechanism 900 may be positioned within the drive housing 408 (FIGS. 4 and 7A-7B).

As illustrated, the unclamp lockout mechanism 900 may include a pawl 902 rotatably mounted to the shaft 402 and, more particularly, to the inner grounding shaft 708 of the shaft 402. The pawl 902 may be received within an aperture 904 defined in the inner grounding shaft 708. In some embodiments, the pawl 902 may provide or otherwise define one or more legs 906 receivable within a corresponding one or more grooves 908 (e.g., u-channels) defined in the inner grounding shaft 708. The pawl 902 may be rotatable (pivotable) about an axis extending through the legs 906.

The unclamp lockout mechanism 900 may further include a biasing device 910 that biases the pawl 902 into the aperture 904 and toward the stowed position. The biasing device 910 may comprise any device or mechanism that provides a biasing (spring) force on the pawl 902. In the illustrated embodiment, for example, the biasing device 910 comprises a ring made of an elastic material (e.g., an O-ring). In other embodiments, however, the biasing device 910 may comprise, but is not limited to, a horseshoe clip, a C-clip, a garter spring, a leaf spring, an extension spring, a torsional spring, a torsion bar, or any combination of the foregoing.

In some embodiments, the biasing device 910 may be seated or otherwise arranged within one or more grooves 912 defined on the shaft 402 (e.g., the inner grounding shaft 708). Locating the biasing device 910 within the groove(s) 912 may help maintain the biasing device 910 axially positioned on the shaft 402. This may prove advantageous during operation and also during manufacturing the device, since locating the biasing device 910 within the groove(s) 912 may help prevent the biasing mechanism from translating axially during manufacture or "walking" during use.

When the pawl 902 is in the stowed position, as shown in FIG. 9A, the closure yoke 726 may be able to move proximally or distally to open or close the jaws 410, 412 (FIG. 4). Moreover, when the pawl 902 is in the stowed position, the cutting element (knife) may be prevented from being displaced distally, which prevents the cutting element from being exposed and potentially causing damage. When the pawl 902 is in the deployed position, as shown in FIG. 9B, the closure yoke 726 may be prevented from moving proximally, thus helping to maintain the jaws 410, 412 closed. With the jaws 410, 412 closed and the pawl 902 in the deployed position, the cutting element may be safely fired. The closure yoke 726 will not be able to move proximally to open the jaws 410, 412 until the cutting element is safely retracted, which allows the pawl 902 to transition back to the stowed position.

Figure 10A:
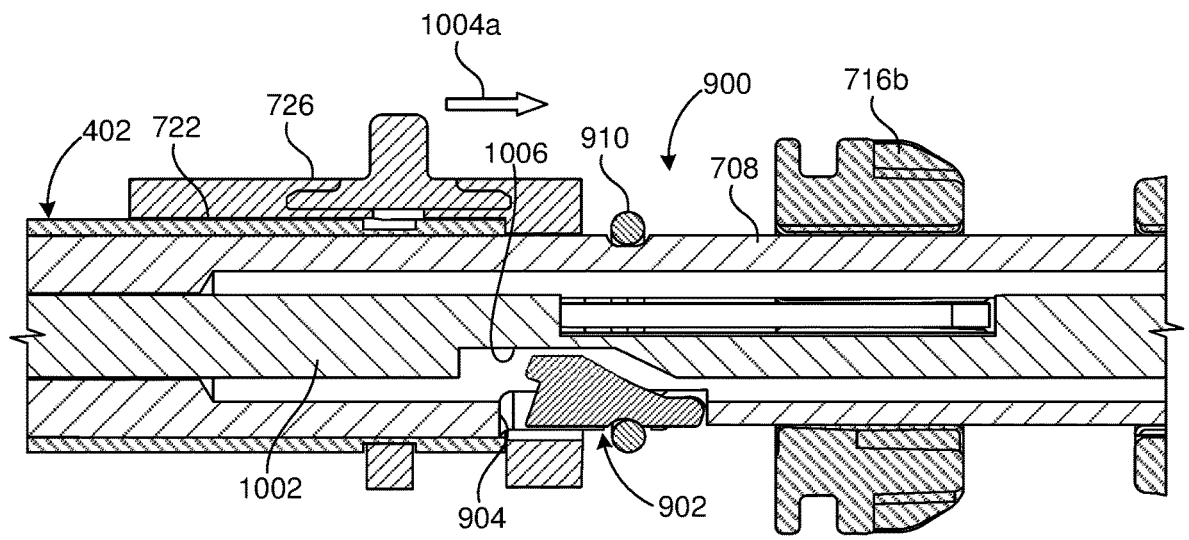
FIGS. 10A-10G are cross-sectional side views of the unclamp lockout mechanism of FIGS. 9A-9B showing progressive operation thereof, according to one or more embodiments of the disclosure.

FIGS. 10A-10G are cross-sectional side views of the unclamp lockout mechanism 900 showing progressive operation thereof, according to the embodiments of the disclosure. Referring first to FIG. 10A, as illustrated, the unclamp lockout mechanism 900 generally interposes the second articulation yoke 716b and the closure yoke 426. A firing rod 1002 extends longitudinally within the shaft 402 and, more particularly, within the inner grounding shaft 708 that extends at least partially within the closure tube 722. As discussed above, the firing rod 1002 may be operatively coupled to the firing member 744 (FIGS. 7A-7B) such that driving the firing member 744 in an axial direction will correspondingly move the firing rod 1002 in the same direction. Moreover, the distal end of the firing rod 1002 may be coupled to the cutting element at the end effector 404 (FIG. 4) such that advancing or retracting the firing rod 1002 will correspondingly advance or retract the cutting element.

In the stowed position, the pawl 902 is received within the aperture 904 defined in the shaft 402 (e.g., the inner grounding shaft 708) and the biasing device 910 may bias the pawl 902 inward to help prevent the pawl 902 from falling out of the aperture 904, such as by gravitational forces. The pawl 902 may be biased to be flush with or otherwise inset into the aperture 904 when in the stowed position, thus allowing the closure yoke 726 and the closure tube 722 to move proximally to a proximal position where the jaws 410, 412 (FIG. 4) open. In the proximal position, the closure yoke 726 and/or the closure tube 722 may extend over and otherwise be radially aligned with at least a portion of the pawl 902.

Moreover, in the stowed position, the pawl 902 may also be received within a cutout 1006 defined in the firing rod 1002. When the pawl 902 is located within the cutout 1006, the firing rod 1002 may be in a retracted position, which correspondingly places the cutting element (or knife) in a home or "homed" position at the end effector 404 (FIG. 4). In the home position, the cutting element is retracted within the end effector 404 to a point where it is not exposed and thus does not present a danger to inadvertent contact.

Figure 10B:
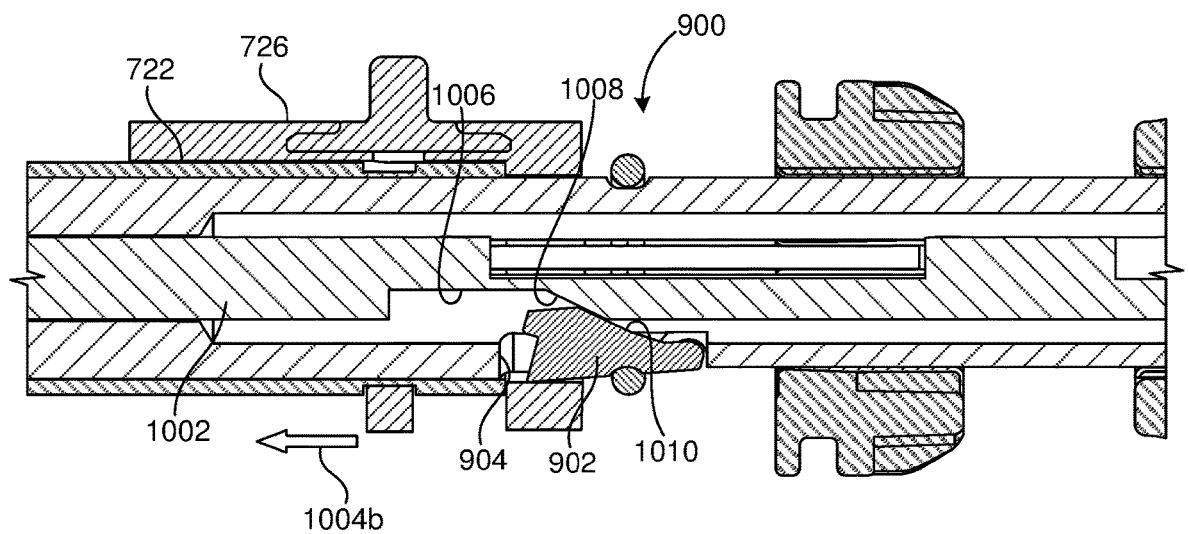

In FIG. 10B, the closure yoke 726 and the interconnected closure tube 722 remain in the proximal position, which allows the jaws 410, 412 (FIG. 4) to be opened. With the closure yoke 726 in the proximal position, any attempt to move the firing rod 1002 distally 1004b to deploy or move the cutting element from the home position will be prevented by the unclamp lockout mechanism 900. More specifically, moving the firing rod 1002 distally 1004b will cause the pawl 902 to engage an endwall 1008 of the cutout 1006. As illustrated, the endwall 1008 may be angled or ramped and the pawl 902 may define an opposing angled surface 1010 engageable with the angled endwall 1008. As the angled endwall 1008 advances distally 1004b and engages the angled surface 1010, the pawl 902 may be urged to pivot radially outward through the aperture 904 and to the deployed position. However, since the closure yoke 726 and/or the closure tube 722 extend over at least a portion of the pawl 902 when in the proximal position, the pawl 902 is prevented from protruding out of the aperture 904. Instead, the pawl 902 may engage an inner radial surface of the closure yoke 726 and/or the closure tube 722, which stops its outward pivoting movement. Consequently, engagement between the endwall 1008 and the pawl 902 axially binds the firing rod 1002 and prevents any further distal 1004b movement, thus preventing the cutting element from moving from the homed position and extending out the open jaws 410, 412 (FIG. 4). As will be appreciated, this may prove advantageous in preventing the cutting element from traversing the end effector 404 with the jaws 410, 412 open.

Figure 10C:
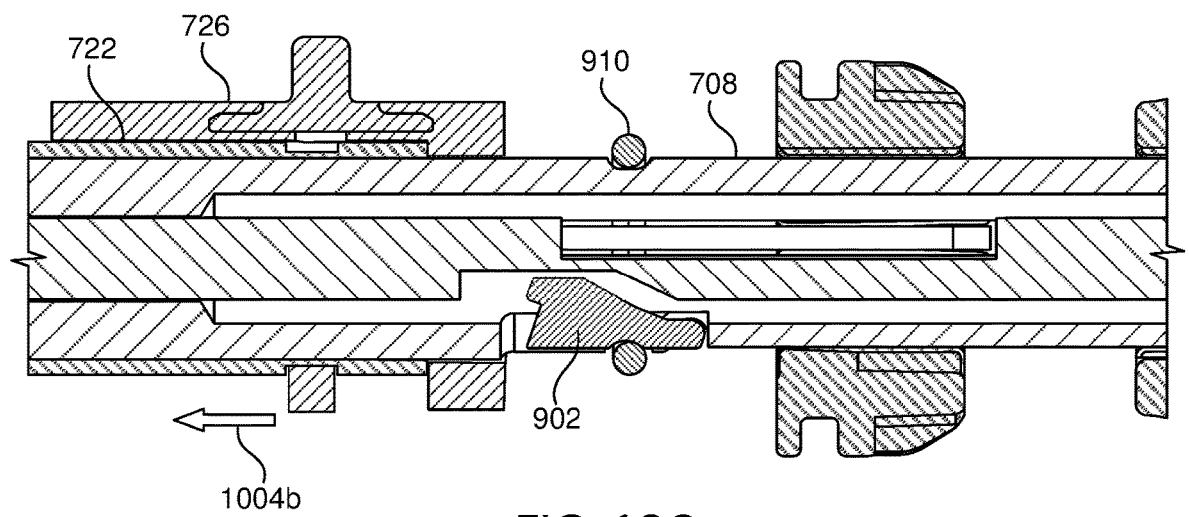

In FIG. 10C, the closure yoke 726 and the interconnected closure tube 722 have been moved distally 1004b relative to the inner grounding shaft 708 and to a distal position, thus causing the jaws 410, 412 (FIG. 4) to be closed at the end effector 404 (FIG. 4). In the distal position, the closure yoke 726 and/or the closure tube 722 are moved away from and otherwise out of radial alignment with the pawl 902, thus allowing the pawl 902 to move (pivot) to the deployed position. The biasing device 910, however, may help maintain the pawl 902 in the stowed position until acted upon to overcome the spring force of the biasing device 910.

Figure 10D:
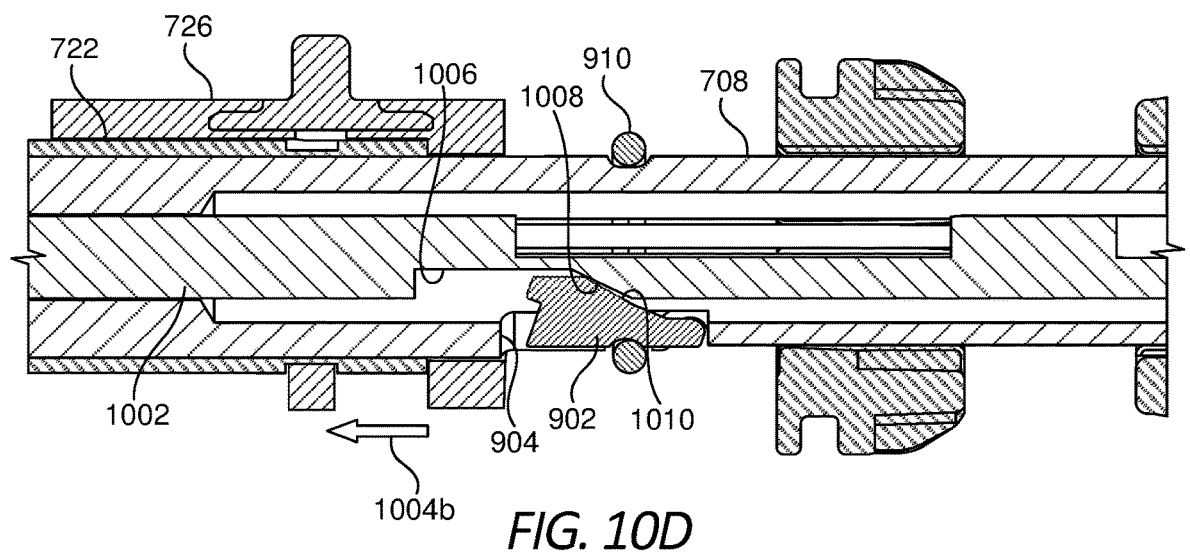

In FIG. 10D, the closure yoke 726 and the interconnected closure tube 722 remain at the distal position to close the jaws 410, 412 (FIG. 4). To fire (distally advance) the cutting element, the firing rod 1002 may be moved distally 1004*b* relative to the inner grounding shaft 708 and the pawl 902. Moving the firing rod 1002 distally 1004*b* will eventually drive the endwall 1008 of the cutout 1006 into axial engagement with the pawl 902 and, more particularly, with the angled surface 1010 of the pawl 902. Further distal movement of the firing rod 1002 will cause the endwall 1008 to slidingly engage the angled surface 1010 and urge the pawl 902 out of the aperture 904 and to the deployed position. The axial load provided by the firing rod 1002 is sufficient to overcome the spring force of the biasing device 910, which allows the pawl 902 to pivot radially outward through the aperture 904.

Figure 10E:
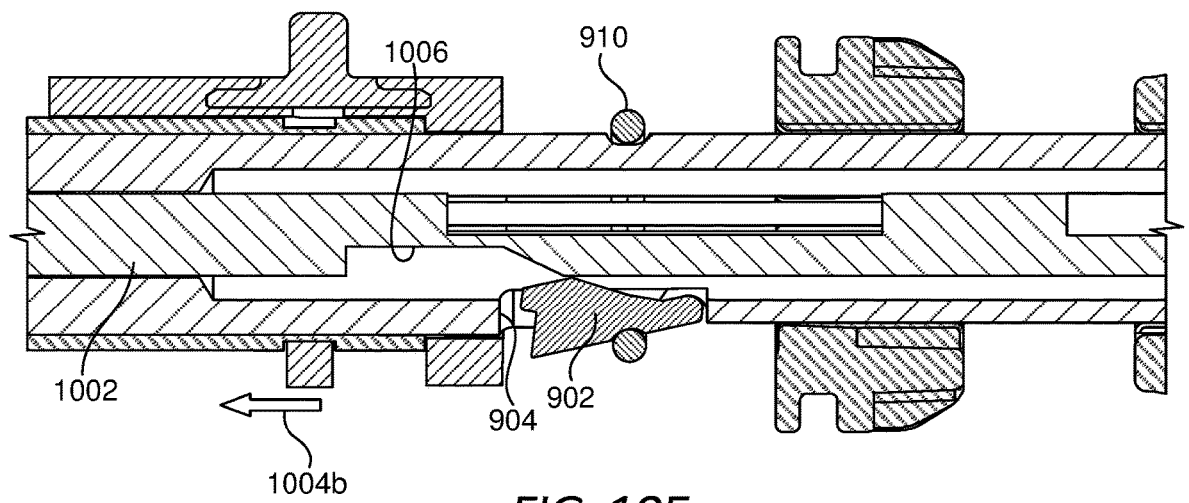

In FIG. 10E, the firing rod 1002 has moved further distally 1004*b* and thereby forced the pawl 902 completely out of the cutout 1006 and to the deployed position. Once the pawl 902 exits the cutout 1006, the biasing device 910 may bias the pawl 902 inward and against the outer surface (contour) of the firing rod 1002. Accordingly, the biasing device 910 may help prevent the pawl 902 from over rotating and otherwise completely falling out of the aperture 904.

Figure 10F:
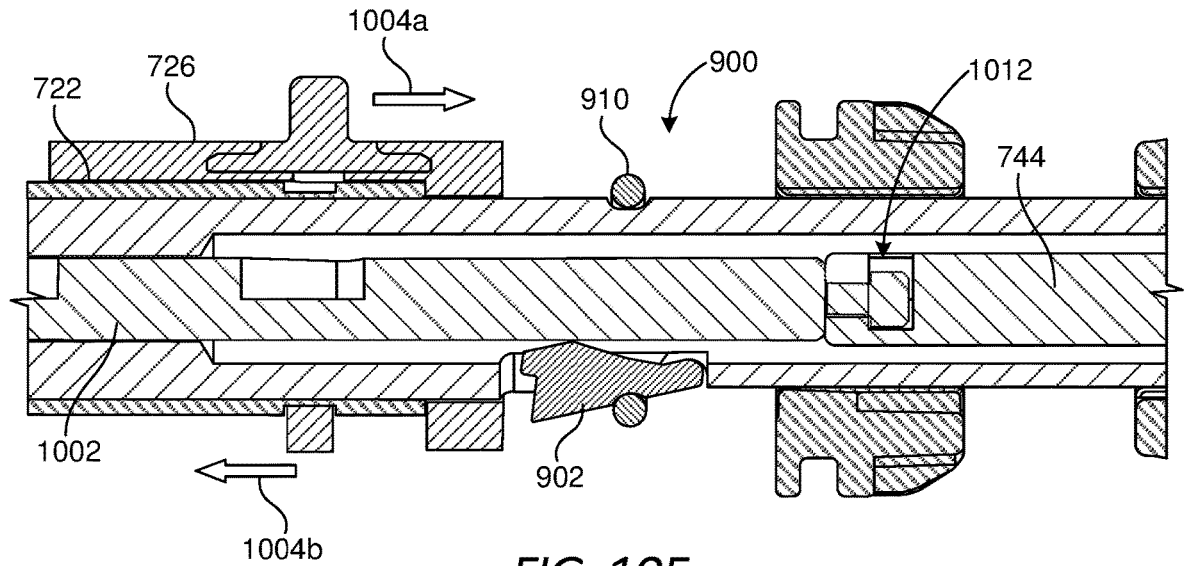

In FIG. 10F, the firing rod 1002 has moved further distally 1004*b* and thereby moved the cutting element at the end effector 404 (FIG. 4) to a fired position. The pawl 902 remains in the deployed position and the biasing device 910 continues to place an inward biasing load on the pawl 902 against the outer surface of the firing rod 1002. FIG. 10F also shows a connection 1012 between the firing rod 1002 and the firing member 744 described above.

In the position shown in FIG. 10F, the jaws 410, 412 (FIG. 4) are closed and the cutting element is fully extended and in the fired position. If the jaws 410, 412 were to open before the cutting element transitions back to the homed position, the cutting element could potentially cause inadvertent tissue damage to a patient, or a user may be inadvertently cut while cleaning the tool. The unclamp lockout mechanism 900 may be configured to prevent the jaws 410, 412 from opening before the cutting element is safely moved back to the home position. More specifically, with the pawl 902 in the deployed position, the closure yoke 726 and the interconnected closure tube 722 may be prevented from returning proximally 1004*a* to the proximal position to open the jaws 410, 412 and expose the cutting element.

Figure 10G:
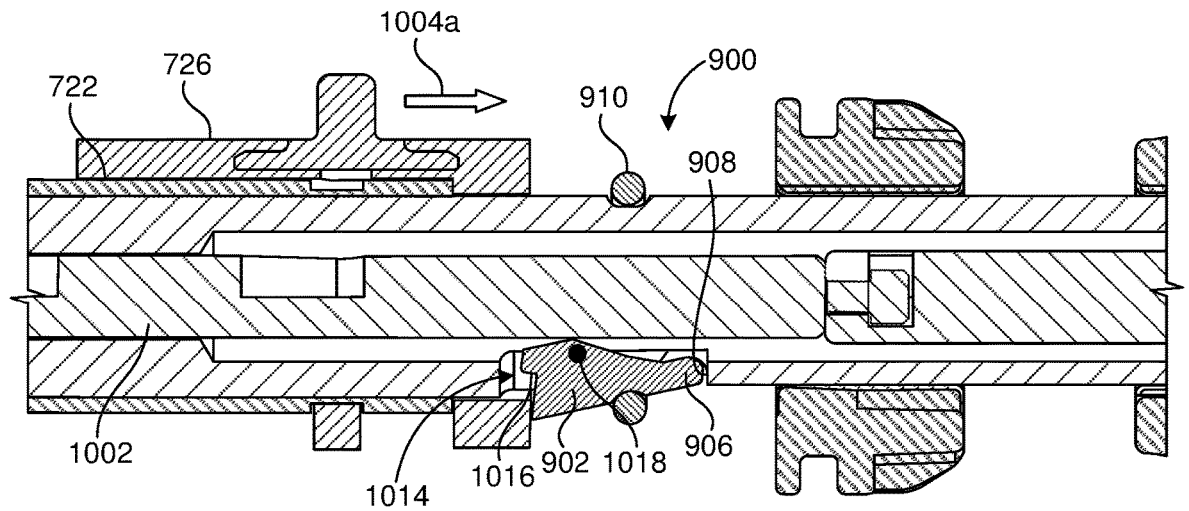

In FIG. 10G, the pawl 902 is biased outwardly by the firing rod 1002 to the deployed position and thereby protrudes out of the aperture 904. If the closure yoke 726 and the interconnected closure tube 722 move proximally 1004*a* in an attempt to move to the proximal position and thereby open the jaws 410, 412 (FIG. 4), the deployed pawl 902 will stop the proximal movement, thus preventing the cutting element from being exposed in the fired position. When the closure yoke 726 and/or the interconnected closure tube 722 axially engage the deployed pawl 902, the axial force applied by the closure yoke 726 will be transmitted to the inner grounding shaft 708 through the pawl 902 via the engagement between the legs 906 of the pawl 902 and the grooves 908 of the inner grounding shaft 708.

If it is desired to open the jaws 410, 412, the firing rod 1002 must first be moved proximally 1004*a* to thereby move the cutting element back to the home position. Moving the firing rod 1002 proximally 1004*a* will also allow the pawl 902 to locate the cutout 1006 (FIGS. 10D-10E), and once located, the biasing device 910 may urge the pawl 902 into the cutout 1006 and back to the stowed position. Once the pawl 902 returns to the stowed position, the closure yoke 726 and the interconnected closure tube 722 may then be moved proximally 1004*a* to the proximal position to open the jaws 410, 412 (FIG. 4) once more.

Still referring to FIG. 10G, in some embodiments, the unclamp lockout mechanism 900 may further include a travel limit feature 1014 that limits the rotation (pivoting movement) of the pawl 902. In one embodiment, as illustrated, the travel limit feature 1014 may comprise a shoulder 1016 defined on the pawl 902, and the shoulder 1016 may be engageable with the closure yoke 726 or a portion of the inner grounding shaft 708 to prevent over rotation of the pawl 902. More specifically, the pawl 902 may have an angled surface that engages the proximal end of the closure yoke 726, and proximal movement of the closure yoke 726 may urge the pawl 902 to rotate further outward at which point the shoulder 1016 engages the inner diameter of the closure yoke 726. In other embodiments, the travel limit feature 1014 may comprise a pin 1018 extending laterally from the pawl 902, and the pin 1018 may also be engageable with a portion of the inner grounding shaft 708 to prevent over rotation of the pawl 902. In yet other embodiments, the travel limit feature 1014 may comprise a pin (not shown) extending proximally from the pawl 902 and engageable with a back side of the inner grounding shaft 708 at its outer diameter.

Figure 11A:
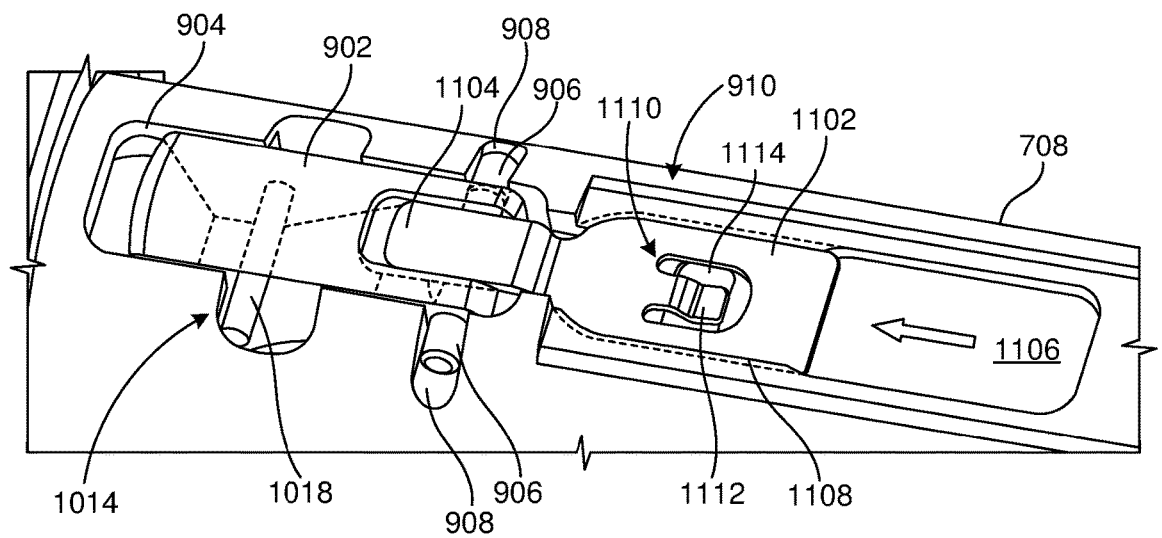
FIGS. 11A and 11B are isometric views of alternative embodiments of the unclamp lockout mechanism of FIGS. 9A-9B and 10A-10G.
Figure 11B:
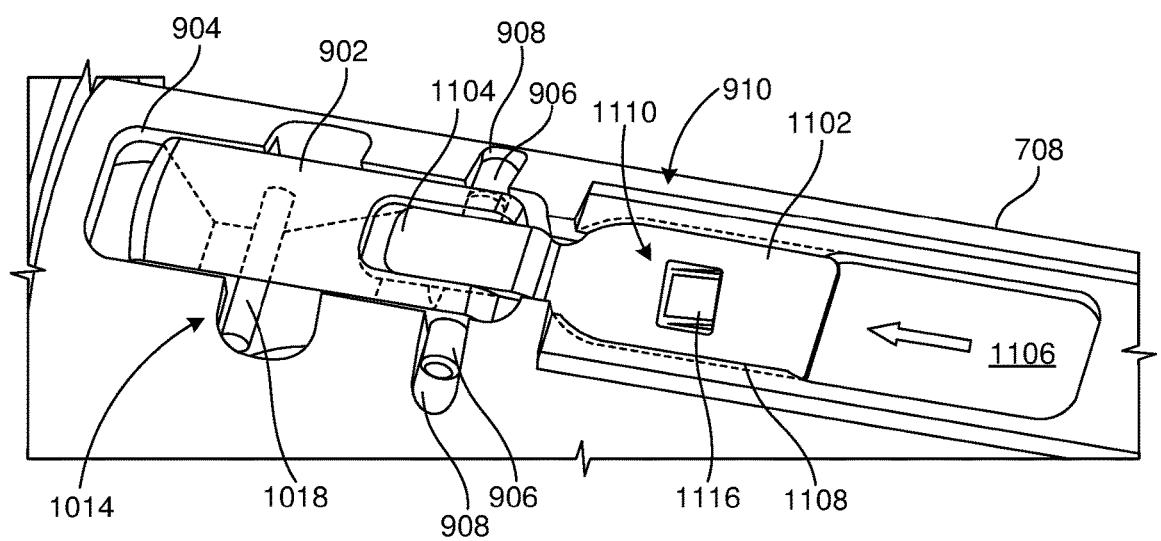

FIGS. 11A and 11B are isometric views of alternative embodiments of the unclamp lockout mechanism 900 and, more particularly of the biasing device 910. As illustrated, the biasing device 910 may comprise a type of leaf spring having a body 1102 and an extension 1104 that extends from the body 1102. The body 1102 may be sized to be received within a depression 1106 defined in the inner grounding shaft 708. Once fitted within the depression 1106, the body 1102 may be moved (e.g., to the left in FIGS. 11A-11B) into a dovetail engagement with the inner grounding shaft 708 where lateral edges of the body 1102 are received beneath longitudinally extending flanges 1108 defined by the depression 1106.

In some embodiments, the body 1102 may be prevented from reversing out of the dovetail engagement with the inner grounding shaft 708 using one or more anti-reverse features 1110. In FIG. 11A, the anti-reverse feature 1110 comprises a downwardly extending tang 1112 that mates with an inset 1114 defined into the depression 1106. The tang 1112 engages an endwall of the inset 1114 to prevent the body 1102 from moving out of the dovetail engagement with the inner grounding shaft 708. In FIG. 11B, the anti-reverse feature 1110 also comprises a downwardly extending tang 1116, but the tang 1116 in FIG. 11B may consist of a punched or bent portion of the body 1102 that extends downwardly into biased engagement with the depression 1106. The spring force provided by the tang 1116 as biased against the depression 1106 helps to maintain the dovetail engagement with the inner grounding shaft 708 and otherwise prevent reversal.

The extension 1104 in each embodiment may be configured to help maintain the pawl 902 generally seated within the aperture 904 defined in the inner grounding shaft 708 until the spring force of the extension 1104 is overcome, such as by the moving firing rod 1002 (FIGS. 10A-10G). As illustrated, the extension 1104 extends over a portion of the pawl 902 and may provide a biasing force the helps keep the legs 906 of the pawl 902 seated within the grooves 908 defined in the inner grounding shaft 708.

Also illustrated in FIGS. 11A and 11B is one embodiment of the travel limit feature 1014 discussed above with reference to FIG. 10G. As illustrated, the travel limit feature 1014 comprises the pin 1018 extending laterally from the pawl 902. The pin 1018 may be engageable with a portion of the inner grounding shaft 708 to prevent over rotation of the pawl 902 out of the aperture 904.

Embodiments disclosed herein include:

A. A surgical tool that includes a drive housing, a shaft that extends from the drive housing, an end effector arranged at an end of the shaft and having opposing jaws and a cutting element, and an unclamp lockout mechanism positioned within the drive housing and including a pawl rotatably mounted to the shaft and positioned proximal to a closure yoke operatively coupled to the shaft, wherein the pawl is pivotable between a stowed position, where the pawl is received within an aperture defined in the shaft, and a deployed position, where the pawl protrudes out of the aperture, and a biasing device that biases the pawl into the aperture and toward the stowed position, wherein, when the pawl is in the stowed position, the closure yoke is movable to a proximal position over at least a portion of the pawl to open the opposing jaws, and wherein, when the pawl is in the deployed position, the closure yoke is prevented from moving to the proximal position.

B. A method of operating a surgical tool, the surgical tool having a drive housing, a shaft extending from the drive housing, and an end effector arranged at an end of the shaft and having opposing jaws and a cutting element, the method including moving a closure yoke operatively coupled to the shaft to a proximal position and thereby opening the opposing jaws, extending the closure yoke over at least a portion of a pawl as the closure yoke moves to the proximal position, the pawl being receivable within an aperture defined in the shaft and rotatably mounted to the shaft, and preventing the cutting element from moving from a home position to a fired position with the pawl when the closure yoke is in the proximal position.

C. An unclamp lockout mechanism for a surgical tool including a pawl rotatably mounted to a shaft of the surgical tool and positioned proximal to a closure yoke operatively coupled to the shaft, wherein the pawl is pivotable between a stowed position, where the pawl is received within an aperture defined in the shaft, and a deployed position, where the pawl protrudes out of the aperture, and a biasing device that biases the pawl into the aperture and toward the stowed position, wherein, when the pawl is in the stowed position, the closure yoke is movable to a proximal position over at least a portion of the pawl to open the opposing jaws, and wherein, when the pawl is in the deployed position, the closure yoke is prevented from moving to the proximal position.

Each of embodiments A, B, and C may have one or more of the following additional elements in any combination: Element 1: wherein the pawl interposes the closure yoke and an articulation yoke operatively coupled to the shaft, and wherein actuation of the articulation yoke causes the end effector to articulate. Element 2: further comprising a firing rod that extends longitudinally within the shaft, wherein, when the pawl is in the stowed position, the pawl is received within a cutout defined by the drive rod and moving the firing rod distally urges the pawl out of the cutout and to the deployed position. Element 3: wherein the cutting element is operatively coupled to a distal end of the firing rod, and when the pawl is received within the cutout, the cutting element is in a home position, and wherein, when the pawl is moved to the deployed position, the cutting element is advanced toward a fired position. Element 4: wherein the cutout defines an angled endwall engageable with the pawl to urge the pawl out of the cutout when the firing rod moves distally. Element 5: wherein, when the closure yoke is in the proximal position, the pawl is prevented from moving to the deployed position and the firing rod is prevented from moving distally to move the cutting element to the fired position. Element 6: wherein the closure yoke is movable to a distal position, where the closure yoke is moved out of radial alignment with the pawl and the opposing jaws are closed. Element 7: wherein the unclamp lockout mechanism further includes a travel limit feature that limits rotation of the pawl, the travel limit feature comprising at least one of a shoulder defined on the pawl and a pin extending from the pawl.

Element 8: wherein preventing the cutting element from moving from the home position to the fired position comprises receiving the pawl within a cutout defined in a firing rod, the cutting element being operatively coupled to a distal end of the firing rod, engaging an endwall of the cutout against the pawl and urging the pawl out of the aperture and to a deployed position, engaging the pawl against an inner diameter of the closure yoke and thereby preventing the pawl from moving to the deployed position, and binding the pawl against the firing rod and thereby preventing the firing rod from moving distally. Element 9: further comprising moving the closure yoke to a distal position, where the closure yoke is moved out of radial alignment with the pawl and the opposing jaws are closed, moving the firing rod distally and thereby moving the cutting element from the home position and toward the fired position, moving the pawl to the deployed position as the firing rod moves distally, and preventing the closure yoke from moving to the proximal position and opening the opposing jaws with the pawl in the deployed position. Element 10: further comprising biasing the pawl into the aperture with a biasing device. Element 11: further comprising limiting rotation of the pawl with a travel limit feature.

Element 12: wherein the pawl provides one or more legs receivable within a corresponding one or more grooves defined in the shaft, and wherein the pawl is rotatable about an axis extending through the one or more legs. Element 13: wherein the biasing device is selected from the group consisting of an elastic ring, a horseshoe clip, a C-clip, a garter spring, a leaf spring, and any combination thereof. Element 14: wherein at least a portion of the biasing device is arranged within a groove defined on the shaft. Element 15: wherein the surgical tool includes a firing rod that extends longitudinally within the shaft, wherein, when the pawl is in the stowed position, the pawl is received within a cutout defined by the drive rod and moving the firing rod distally urges the pawl out of the cutout and to the deployed position. Element 16: wherein the cutting element is operatively coupled to a distal end of the firing rod, and when the pawl is received within the cutout, the cutting element is in a home position, and wherein, when the pawl is moved to the deployed position, the cutting element is advanced toward a fired position. Element 17: wherein, when the closure yoke is in the proximal position, the pawl is prevented from moving to the deployed position and the firing rod is prevented from moving distally to move the cutting element to the fired position.

By way of non-limiting example, exemplary combinations applicable to A, B, and C include: Element 2 with Element 3; Element 3 with Element 4; Element 4 with Element 5; Element 8 with Element 9; Element 15 with Element 16; and Element 15 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing;
   a shaft that extends from the drive housing;
   an end effector arranged at an end of the shaft and having opposing jaws and a cutting element; and
   an unclamp lockout mechanism positioned within the drive housing and including:
     a pawl rotatably mounted to the shaft and positioned proximal to a closure yoke operatively coupled to the shaft, wherein the pawl is pivotable between a stowed position, where the pawl is received within an aperture defined in the shaft, and a deployed position, where the pawl protrudes out of the aperture; and
     a biasing device that biases the pawl into the aperture and toward the stowed position,
   wherein, when the pawl is in the stowed position, the closure yoke is movable to a proximal position over at least a portion of the pawl to open the opposing jaws, and
   wherein, when the pawl is in the deployed position, the closure yoke is prevented from moving to the proximal position.

2. The surgical tool of claim 1, wherein the pawl interposes the closure yoke and an articulation yoke operatively coupled to the shaft, and wherein actuation of the articulation yoke causes the end effector to articulate.

3. The surgical tool of claim 1, further comprising a firing rod that extends longitudinally within the shaft, wherein, when the pawl is in the stowed position, the pawl is received within a cutout defined by the firing rod and moving the firing rod distally urges the pawl out of the cutout and to the deployed position.

4. The surgical tool of claim 3, wherein the cutting element is operatively coupled to a distal end of the firing rod, and when the pawl is received within the cutout, the cutting element is in a home position, and wherein, when the pawl is moved to the deployed position, the cutting element is advanced toward a fired position.

5. The surgical tool of claim 4, wherein the cutout defines an angled endwall engageable with the pawl to urge the pawl out of the cutout when the firing rod moves distally.

6. The surgical tool of claim 5, wherein, when the closure yoke is in the proximal position, the pawl is prevented from moving to the deployed position and the firing rod is prevented from moving distally to move the cutting element to the fired position.

7. The surgical tool of claim 1, wherein the closure yoke is movable to a distal position, where the closure yoke is moved out of radial alignment with the pawl and the opposing jaws are closed.

8. The surgical tool of claim 1, wherein the unclamp lockout mechanism further includes a travel limit feature that limits rotation of the pawl, the travel limit feature comprising at least one of a shoulder defined on the pawl and a pin extending from the pawl.

9. A method of operating a surgical tool, the surgical tool having a drive housing, a shaft extending from the drive housing, and an end effector arranged at an end of the shaft and having opposing jaws and a cutting element, the method comprising:
   moving a closure yoke operatively coupled to the shaft to a proximal position and thereby opening the opposing jaws;
   extending the closure yoke over at least a portion of a pawl as the closure yoke moves to the proximal position, the pawl being receivable within an aperture defined in the shaft and rotatably mounted to the shaft; and
   preventing the cutting element from moving from a home position to a fired position with the pawl when the closure yoke is in the proximal position.

10. The method of claim 9, wherein preventing the cutting element from moving from the home position to the fired position comprises:
   receiving the pawl within a cutout defined in a firing rod, the cutting element being operatively coupled to a distal end of the firing rod;
   engaging an endwall of the cutout against the pawl and urging the pawl out of the aperture and to a deployed position;

engaging the pawl against an inner diameter of the closure yoke and thereby preventing the pawl from moving to the deployed position; and binding the pawl against the firing rod and thereby preventing the firing rod from moving distally.

11. The method of claim 10, further comprising:

moving the closure yoke to a distal position, where the closure yoke is moved out of radial alignment with the pawl and the opposing jaws are closed;

moving the firing rod distally and thereby moving the cutting element from the home position and toward the fired position;

moving the pawl to the deployed position as the firing rod moves distally; and preventing the closure yoke from moving to the proximal position and opening the opposing jaws with the pawl in the deployed position.

12. The method of claim 9, further comprising biasing the pawl into the aperture with a biasing device.

13. The method of claim 9, further comprising limiting rotation of the pawl with a travel limit feature.

14. An unclamp lockout mechanism for a surgical tool, comprising:

a pawl rotatably mounted to a shaft of the surgical tool and positioned proximal to a closure yoke operatively coupled to the shaft, wherein the pawl is pivotable between a stowed position, where the pawl is received within an aperture defined in the shaft, and a deployed position, where the pawl protrudes out of the aperture; and a biasing device that biases the pawl into the aperture and toward the stowed position, wherein, when the pawl is in the stowed position, the closure yoke is movable to a proximal position over at least a portion of the pawl to open the opposing jaws of the surgical tool, and wherein, when the pawl is in the deployed position, the closure yoke is prevented from moving to the proximal position.

15. The unclamp lockout mechanism of claim 14, wherein the pawl provides one or more legs receivable within a corresponding one or more grooves defined in the shaft, and wherein the pawl is rotatable about an axis extending through the one or more legs.

16. The unclamp lockout mechanism of claim 14, wherein the biasing device is selected from the group consisting of an elastic ring, a horseshoe clip, a C-clip, a garter spring, a leaf spring, and any combination thereof.

17. The unclamp lockout mechanism of claim 14, wherein at least a portion of the biasing device is arranged within a groove defined on the shaft.

18. The unclamp lockout mechanism of claim 14, wherein the surgical tool includes a firing rod that extends longitudinally within the shaft, wherein, when the pawl is in the stowed position, the pawl is received within a cutout defined by the firing rod and moving the firing rod distally urges the pawl out of the cutout and to the deployed position.

19. The unclamp lockout mechanism of claim 18, wherein the cutting element is operatively coupled to a distal end of the firing rod, and when the pawl is received within the cutout, the cutting element is in a home position, and wherein, when the pawl is moved to the deployed position, the cutting element is advanced toward a fired position.

20. The unclamp lockout mechanism of claim 18, wherein, when the closure yoke is in the proximal position, the pawl is prevented from moving to the deployed position and the firing rod is prevented from moving distally to move the cutting element to the fired position.

\* \* \* \* \*